United States Patent [19]

Maish

[11] Patent Number: 4,983,399

[45] Date of Patent: Jan. 8, 1991

[54] DIRECT COMPRESSION CARRIER COMPOSITION

[75] Inventor: Shabir Z. Maish, Kingsport, Tenn.

[73] Assignee: Eastman Kodak Company, Rochester, N.Y.

[21] Appl. No.: 423,157

[22] Filed: Oct. 18, 1989

[51] Int. Cl.$^5$ ................................................. A61K 9/20
[52] U.S. Cl. ..................... 424/465; 424/464; 536/32; 106/181; 106/183
[58] Field of Search ............... 106/169, 178, 181, 183; 424/489, 468, 469, 470, 465; 536/32

[56] References Cited

U.S. PATENT DOCUMENTS

| | | | |
|---|---|---|---|
| 3,146,168 | 8/1964 | Battista | 167/82 |
| 3,146,170 | 8/1964 | Battista | 167/85 |
| 4,590,062 | 5/1986 | Jang | 424/19 |
| 4,834,985 | 5/1989 | Elger | 424/488 |

FOREIGN PATENT DOCUMENTS

WO84/00807 12/1984 PCT Int'l Appl.

OTHER PUBLICATIONS

*Pharmaceutical Dosage Forms*, vol. 1, pp. 147–164.

Primary Examiner—Thurman K. Page
Attorney, Agent, or Firm—J. Frederick Thomsen; William P. Heath, Jr.

[57] ABSTRACT

Disclosed is a direct compression carrier composition comprising one or more cellulose carboxylic acid esters and a lubricant useful in the preparation of tablets containing a physiologically active compound. Also disclosed are direct compression tableting compositions comprising the aforesaid direct compression carrier composition and a medicament and medicinal tablets prepared therefrom.

20 Claims, No Drawings

DIRECT COMPRESSION CARRIER COMPOSITION

This invention pertains to a direct compression carrier composition useful in the preparation of tablets containing a physiologically active compound. More particularly, this invention pertains to direct compression compositions comprising one or more cellulose carboxylic acid esters and to combinations of the direct compression compositions containing a physiologically active substance or compound and to tablets produced therefrom.

Compressed medicinal dosage forms, commonly referred to as tablets, typically are made by compaction of a blend of one or more physiologically active compounds, inert diluents, binders, colorants, flavors, sweeteners, buffering agents, lubricants, disintegrants and agents which promote the solubility, erosion and release of the physiologically-active ingredient. Very few drugs and diluents have a crystalline structure which allows a dry blend thereof to flow freely, a characteristic which is essential to the preparation of tablets. Furthermore, few combinations of physiologically-active compounds and diluents possess the inherent cohesive properties and compressibility required to compress them into tablets of diverse shapes and sizes. The free flow and compressibility characteristics of blends of dry ingredients is very critical to the manufacture of tablets having a uniform size and weight and a degree of hardness within a narrow range.

The term "direct compression" is used herein to refer to the process by which tablets are compressed directly from powder blends of the active ingredients, i.e., a physiologically-active substance, and suitable excipients, including fillers, disintegrants and lubricants, which will flow uniformly into a die cavity to form a firm tablet. No pretreatment of the powder blends by wet or dry granulation procedures is necessary. The development of and the advantages offered by direct compression carrier compositions in the manufacture of tablets is presented by H. A. Lieberman and L. Lachman in Pharmaceutical Dosage Forms, Vol. 1, pages 147-173, Marcel Dekker, Inc., New York (1980).

A specially processed form of microcrystalline cellulose sold under the name Avicel is one of the most widely used direct compression carriers and is considered to be the reference standard for direct compression carriers. U.S. Pat. No. 2,978,446 discloses the preparation of microcrystalline cellulose by the controlled acid hydrolysis of cellulose to fragment the fibrous structure into small crystalline aggregates of a specific degree of polymerization. U.S. Pat. No. 3,146,168 refers to the use of microcrystalline cellulose in the preparation of pharmaceutical preparations including direct compression tableting. Although such microcrystalline cellulose possesses excellent compressibility properties, it suffers from poor fluidity (flowability) which presents problems in die filling and blending with some physiologically-active compounds. Furthermore, the carrying capacity of microcrystalline cellulose is limited to about 40 weight percent, i.e., the maximum amount of physiologically-active compound which can be blended with microcrystalline cellulose is approximately 40 weight percent based on the weight of the blend.

The direct compression carrier composition provided by the present invention comprises a compressible, free-flowing particulate composition comprising (1) a cellulose carboxylic acid ester powder having a certain particle size distribution, particle mean diameter and bulk density and (2) a lubricant. The cellulose ester particles of the composition of this invention have a mean diameter in the range of about 70 to 200 microns and a bulk density in the range of about 0.2 to 0.6 grams per mL (g/mL). The particle size distribution of the cellulose ester powder is such that the cumulative weight percent of the cellulose ester powder retained on Number 60, 80, 100, 120, 140 and 200 sieves is:

| Sieve Number | Cumulative Weight Percent Retained |
|---|---|
| 60 | about 5 to 30 |
| 80 | about 10 to 40 |
| 100 | about 20 to 60 |
| 120 | about 36 to 75 |
| 140 | about 45 to 85 |
| 200 | about 60 to 92 | and the weight percent of cellulose ester powder which passes through a Number 325 sieve is not more than about 12 weight percent. The above sieve numbers are U.S. sieves series and correspond to international (ISO) standards.

The direct compression carrier compositions provided by this invention possess an excellent combination of properties such as compressibility, fluidity and carrying capability. The compositions may be compressed into hard tablets with minimum friability using conventional tableting equipment and moderate compression forces in the range of 2000 to 3000 pounds per square inch (psi). Tablet friability is an indirect measure of the degree of bonding between the particles of the medicament and the direct compression carrier composition under compression force. Tablet friability is generally considered to be acceptable if a tablet does not lose more than 1% of its weight in the form of fine particles when subjected to tumbling stress. The carrying capability of a direct compression carrier composition refers to the amount of medicament which may be combined with the carrier composition to produce tablets having acceptable properties, e.g., friability and disintegration. For example, I have found that tablets containing greater than about 40 weight percent of acetaminophen, an analgesic drug known to pose compressibility, friability and tablet ejection problems, can be produced from my novel direct compression carrier composition.

The direct compression carrier composition of this invention may be used in combination with other known carrier materials such as microcrystalline cellulose, starch, calcium phosphate, dextrose, lactose and the like. Normally, at least 30 weight percent, preferably at least 50 weight percent, of the direct compression carrier composition is comprised of the cellulose ester particulate material described herein.

The cellulose esters which may be used in accordance with my invention are esters of cellulose and residues of carboxylic acids having 2 to about 4 carbon atoms having a degree of esterification of about 1 to 3.0 per anhydroglucose unit. Cellulose acetate, cellulose propionate, cellulose acetate propionate and cellulose acetate butyrate are examples of such cellulose esters. The preferred cellulose esters are cellulose acetate esters having a degree of esterification of about 1.6 to 3.0, particularly cellulose acetates having a viscosity of about 10 to 300 poises determined by ASTM Procedures D817 (Formula A) and D1343 and an acetyl content of about 22 to 44 weight percent.

The direct compression carrier compositions provided by this invention include a lubricant which may be any lubricant compound or compositions commonly used in tableting compositions. The function of the lubricant in my novel compositions is to promote the fluidity (flowability) of the compositions, to aid in the release of tablets from the die in the manufacture of tablets and to promote uniform distribution of the active and inert components in the compositions. Examples of such lubricants include talc; saturated fatty acids having about 16 to 20 carbon atoms, e.g., stearic acid; magnesium and calcium salts of saturated fatty acids having about 16 to 20 carbon atoms, e.g., magnesium and calcium stearate; alkali metal salts of aromatic carboxylic acids such as sodium and potassium benzoate; silica, e.g., colloidal silica available under the name Cab-O-Sil; high molecular weight poly(alkylene glycols) such as high molecular weight poly(ethylene glycol); and silicones. Other lubricants which may be used include monoesters of propylene glycol and a saturated fatty acid containing about 8 to 22, preferably 16 to 20, carbon atoms, especially propylene glycol monostearate; monoglycerides and mixtures of mono- and di-glycerides having an iodine number of not more than 15; alkali metal salts of esters of lactic acid and a saturated fatty acid containing about 8 to 22, preferably 16 to 20, carbon atoms, especially sodium stearoyl lactylate; and mixtures of such compounds. The monoglycerides and mono/diglyceride mixtures comprise monoesters and mixtures of mono- and di-esters of glycerin and one or more saturated fatty acids having about 8 to 22, preferably 16 to 20, carbon atoms. The propylene glycol monoesters and glycerides typically are prepared from naturally-occurring materials such as animal and vegetable fats, including hydrogenated derivatives thereof, and therefore may consist of a mixture of specific compounds. Normally, these esters are of at least 90% purity, i.e., at least 90% monoesters or mono/diesters.

The amount of lubricant present in the direct compression carrier compositions may be varied substantially depending, for example, on the particular lubricant and cellulose ester employed, the presence of other ingredients in the composition and the physiologically-active compound (medicament) and the amount thereof for which the carrier composition is designed. Typically the amount of lubricant present is in the range of about 0.25 to 5.0 weight percent based on the total weight of the compositions with concentrations of about 0.5 to 2.0 weight percent being more common. The lubricant component is in the form of a fine powder, e.g., a powder having a particle size such that at least 90 weight percent of the particles pass a number 120 sieve. Preferably, at least 90 weight percent of the lubricant powder employed passes a number 200 sieve.

A particularly preferred lubricant comprises a mixture of:

(i) about 20 to 40 weight percent of monoglycerides or mono/diglyceride mixture having an iodine number of about 2 to 15;

(ii) about 40 to 70 weight percent of a monoester of propylene glycol and a saturated fatty acid having about 16 to 20 carbon atoms;

(iii) about 5 to 20 weight percent of an alkali metal salt of an ester of lactic acid and a saturated fatty acid having about 16 to 20 carbon atoms; and (iv) up to about 10 weight percent silica, e.g., amorphous, fumed or colloidal silica; based on the total weight of the lubricant composition.

The above-described preferred lubricant compositions may be prepared by melt blending commercially-available materials until a homogeneous mass is obtained and then forming a powder from the mass. Melt blending may be accomplished by individually maintaining or raising the temperature of the compounds to a point above their respective melting temperatures so that each is a molten mass and then thoroughly blending, or by mixing the ingredients at ambient temperature and then raising the temperature of the mixture to the melting point of the highest-to-melt ingredient followed by thorough blending to form a homogeneous melt. Preferably, melt blending is carried out at a temperature in the range of about 80° to 120° C. Powdering may be accomplished by conventional means such as, for example, spray chilling, freezing and pulverizing, or by any other means known in the art. Experimental quantities of the lubricant blend may be prepared by rapidly stirring a melt of the ingredients in a beaker to obtain a homogeneous blend, allowing the melt blend to solidify and then pulverizing the solid blend in the presence of dry ice using a high speed stirring device such as a Waring Blender. The lubricant composition thus obtained is a white, free-flowing powder which, if necessary, can be classified using one or more sieves to a particle size in the range of 50 to 300 microns.

The direct compression carrier compositions may also include a minor amount of a wetting agent such as an alkali metal salt of a sulfate of a saturated aliphatic alcohol containing about 8 to 22 carbon atoms, especially sodium lauryl sulfate. The wetting agent may be present in a concentration of up to about 1.0, preferably about 0.2 to 0.6, weight percent based on the weight of the composition.

A direct compression carrier composition provided by this invention which is especially preferred comprises:

I. cellulose acetate having a degree of esterification of about 2.2 to 2.6, a viscosity of about 30 to 150 poises and an acetyl content of about 35 to 42 weight percent, in the form of a powder having a mean particle size of about 120 to 200 microns, a bulk density of about 0.3 to 0.4 and a particle size distribution which gives a screen analysis in terms of the cumulative weight percent of the powder retained on Number 60, 80, 100, 120, 140 and 200 sieves of:

| Sieve Number | Cumulative Weight Percent Retained |
|---|---|
| 60 | about 5 to 15 |
| 80 | about 25 to 35 |
| 100 | about 35 to 55 |
| 120 | about 45 to 65 |
| 140 | about 55 to 75 |
| 200 | about 65 to 85 | and the weight percent of cellulose ester powder which passes through a Number 325 sieve is not more than about 7 weight percent; and II. about 0.5 to 2.0 weight percent, based on the weight of the direct compression carrier composition, of a lubricant composition comprising:

(i) about 25 to 35 weight percent of monoglycerides or mono/diglyceride mixture having an iodine number of about 2 to 15;

(ii) about 50 to 60 weight percent of a monoester of propylene glycol and a saturated fatty acid having about 16 to 20 carbon atoms;

(iii) about 12 to 18 weight percent of an alkali metal salt of an ester of lactic acid and a saturated fatty acid having about 16 to 20 carbon atoms; and (iv) up to about 5 weight percent silica;

based on the total weight of the lubricant composition.

This invention also includes a direct compression tableting composition comprising (1) the above-described direct compression carrier composition and (2) a physiologically-active compound, i.e., a medicament, and medicinal tablets produced therefrom. The tableting compositions preferably contain up to about 1.0, especially 0.2 to 0.6, weight percent of the wetting agent described hereinabove. The medicament may be any normally-solid, physiologically-active compound, substance or material such as, for example, aspirin (acetylsalicylic acid), acetaminophen (p-acetamidophenol) and aluminum hydroxide. My invention is particularly suitable for use in the preparation of tablets containing high concentrations, e.g., greater than 40 weight percent based on the weight of the tablet, of one or more medicaments.

The direct compression carrier and tableting compositions and tablets produced therefrom provided by this invention are further illustrated by the following examples. The cellulose ester used in the examples has a degree of esterification of 2.4, a viscosity of 38 poises and an acetyl content of 40 weight percent and is available as Cellulose Acetate 398-10 from Eastman Chemical Products, Inc. The cellulose acetate is in the form of a powder having a mean particle size of 130 to 170 microns, a loose density of 0.29 to 0.33 g/mL, a bulk density of 0.35 to 0.42 g/mL and a particle size distribution which gives a screen analysis in terms of the cumulative weight percent of the powder retained on Number 10, 20, 40, 60, 80, 100, 120, 140 and 200 sieves of:

| Sieve Number | Cumulative Weight Percent Retained |
|---|---|
| 10 | 0.00 |
| 20 | 0.02 |
| 40 | 1.15 |
| 60 | 11.91 |
| 80 | 29.70 |
| 100 | 46.00 |
| 120 | 56.00 |
| 140 | 67.00 |
| 200 | 79.00 |
| 325 | 93.00 |

The "lubricant" used is a composition comprised of 49 weight percent propylene glycol monostearate, 36 weight percent of a monoglyceride comprised primarily of glycerin monostearate and having and iodine number of not greater than about 6, 11 weight percent sodium stearoyl lactylate and about 4 weight percent amorphous silica.

The powder blends described in the examples are prepared in a V-Blender equipped with an intensifier bar and the tablets are prepared with a Manesty D3 tablet press using the compression and tablet ejection forces specified. Mean diameter (microns), loose density (g/mL), bulk density (g/mL), tablet hardness (Newtons), tablet friability (weight percent) and tablet disintegration are determined in accordance with United States Pharmacopeia XXII procedures and bioavailability is determined according to U.S. FDA guidelines.

EXAMPLES 1–6

Six direct compression carrier compositions are prepared by blending the cellulose acetate powder and lubricant composition described above, sodium lauryl sulfate (SLS), and, optionally, starch, lactose, dextrose, microcrystalline cellulose (Avicel), microcrystalline cellulose and/or dicalcium orthophosphate (CaHPO$_4$, Ca phosphate) for approximately 45 minutes. The SLS, starch, lactose, dextrose, micro cellulose and Ca phosphate employed are in the form of powders which pass a number 60 sieve. The compositions, by weight percent, of Examples 1–6 are shown in Table I.

TABLE I

| Ingredient | Example | | | | | |
|---|---|---|---|---|---|---|
| | 1 | 2 | 3 | 4 | 5 | 6 |
| Cellulose Ester | 40.0 | 50.0 | 70.0 | 80.0 | 97.5 | 70.0 |
| Lubricant | 2.0 | 5.0 | 1.0 | 3.0 | 2.0 | 2.0 |
| SLS | 0.5 | 0.5 | 0.5 | 0.5 | 0.5 | 0.0 |
| Starch | 20.0 | 17.5 | 11.5 | 5.0 | 0.0 | 10.0 |
| Lactose | 0.0 | 10.0 | 0.0 | 5.0 | 0.0 | 3.0 |
| Dextrose | 0.0 | 10.0 | 2.0 | 2.0 | 0.0 | 2.0 |
| Micro Cellulose | 10.0 | 0.0 | 10.0 | 0.0 | 0.0 | 8.0 |
| Ca Phosphate | 27.5 | 7.0 | 5.0 | 4.5 | 0.0 | 5.0 |

EXAMPLE 7

A direct compression tableting composition is prepared by blending acetaminophen powder USP (2549.4 g), the direct compression carrier composition of Example 5 (4318.6 g) and sodium starch glycolate tablet disintegrant (132.0 g) purchased as Ac-di-Sol for 4 minutes. The resulting composition is loaded into the hopper of a Manesty D3 tablet press and 9881 tablets are manufactured using a compression force of 1000 to 4000 psi. Each tablet weighs 687.5±20.7 mg, is 5.8 mm thick and contains 258±13 mg acetaminophen. The hardness (Newtons), tablet ejection force (psi), friability (weight percent) and disintegration time (seconds) of the tablets compressed at 1000, 2000, 3000 and 4000 psi are shown in Table II. The tablets released 100% of the acetaminophen in 20 minutes in gastric fluid at 50 revolutions per minute according to the USP dissolution test.

EXAMPLE 8

The procedure described in Example 7 is repeated using acetaminophen powder USP (4248.0 g), the direct compression carrier composition of Example 5 (4248.0 g) and sodium starch glycolate disintegrant (132.0 g) Each tablet weighs 708i20 mg, is 5.9 mm thick and contains 348±14 mg acetaminophen. The hardness (Newtons), tablet ejection force (psi), friability (weight percent) and disintegration time (seconds) of the tablets compressed at 1000, 2000, 3000 and 4000 psi are shown in Table II. The tablets released 100% of the acetaminophen in 20 minutes in gastric fluid at 50 revolutions per minute according to the USP dissolution test.

TABLE II

| | Tablet Compression Force (psi) | | | |
|---|---|---|---|---|
| | 1000 | 2000 | 3000 | 4000 |
| Example 7 | | | | |
| Hardness | 172 | 259 | 280 | 281 |
| Ejection force | 60 | 50 | 40 | 40 |

TABLE II-continued

| | Tablet Compression Force (psi) | | | |
|---|---|---|---|---|
| | 1000 | 2000 | 3000 | 4000 |
| Friability | 1.60 | 0.60 | 0.48 | 0.48 |
| Disintegration | 30 | 70 | 54 | 91 |
| Example 8 | | | | |
| Hardness | 80 | 120 | 135 | 157 |
| Ejection force | 80 | 80 | 90 | 90 |
| Friability | 2.90 | 1.60 | 1.60 | 1.30 |
| Disintegration | 20 | 43 | 102 | 111 |

Tablets cannot be successfully manufactured, i.e., a coherent tablet cannot be obtained, according to the procedure of Examples 7 and 8 when the direct compression carrier composition used in those examples is replaced with identical amounts of a carrier composition consisting of 98 weight percent microcrystalline cellulose (Avicel) and 2 weight percent of magnesium stearate lubricant.

EXAMPLE 9

A direct compression tableting composition is prepared by blending aspirin powder USP (500.0 g), the direct compression carrier composition of Example 5 (510.0 g) and 40.0 g of lubricant for 4 minutes. Tablets are manufactured in a Manesty D3 tablet press using 4-0.25 inch punches and compression forces of 1100, 2100, 3200 and 4200 psi. Each tablet weighs 867±8.6 mg and contains 413±12 mg aspirin. The hardness (Newtons), die ejection force (psi), time of disintegration (minutes) and friability (weight percent) of the tablets compressed at 1100, 2100, 3200 and 4200 psi are shown in Table III. The tablets have an average thickness of 6.95 mm.

TABLE III

| | Tablet Compression Force (psi) | | | |
|---|---|---|---|---|
| | 1100 | 2100 | 3200 | 4200 |
| Hardness | 160 | 189 | 209 | 213 |
| Ejection force | 45 | 45 | 50 | 50 |
| Disintegration | 1.5 | 4.0 | 6.0 | 7.0 |
| Friability | 0.2 | 0.2 | 0.2 | 0.2 |

EXAMPLE 10

The tablets produced in Example 7 at a compression force of 2500 psi are evaluated for their efficacy by administering 2 tablets to nine normal, healthy human males after an overnight fast. Blood samples are collected at 0.0, 0.25, 0.50, 0.75, 1.0, 1.50, 2.00, 2.50, 4.0, 6.0, 8.0, 10.0, 12.0, 16.0 and 24.0 hours after administration of the tablet and frozen until analysis by high pressure chromatography. The evaluation includes the administration of 2 tablets identical to the Example 7 tablets but manufactured from a composition in which the cellulose acetate is replaced with microcrystalline cellulose (Avicel). The results are shown in Table IV wherein AUC represents the area under the blood level-time curve, a measure of the extent of absorption (mcg/mL X hour); CMAX represents the peak blood level (mcg/mL) of acetaminophen, a measure of the rate of absorption and related therapeutic value; and TMAX represents the time to reach peak blood level (hours), a measure of the onset of action and rate of absorption. PCT >75 is the percent of subjects having values greater than 75% of the mean, TREAT F and PR >F are known statistical parameters and POWER refers to the ability of the evaluation to discriminate the false observation error from the real value.

TABLE IV

| | Example 7 Tablets Mean | Avicel Tablets Mean | PCT > 75 | TREAT F | PR > F | POWER |
|---|---|---|---|---|---|---|
| AUC | 20.93 | 22.07 | 100 | 1.95 | 0.21 | 0.98 |
| CMAX | 6.15 | 6.52 | 89 | 0.72 | 0.42 | 0.98 |
| TMAX | 0.72 | 0.50 | 22 | 2.21 | 0.18 | 0.35 |

The tablets do not cause gastric bleeding or irritation as established by negative occult blood analyses of fecal samples collected before dosing and after the collection of the last blood sample. A subjective evaluation of the subjects establishes that no nausea or other undesirable effects are experienced.

The invention has been described in detail with particular reference to preferred embodiments thereof, but it will be understood that variations and modifications may be effected within the spirit and scope of the invention.

I claim:

1. A direct compression carrier composition comprising a compressible, free-flowing particulate composition comprising (1) at least 30 weight percent of a powder of an ester of cellulose and residues of carboxylic acids having 2 to 4 carbon atoms having a degree of esterification of about 1.0 to 3.0 having a mean diameter of about 70 to 200 microns, a bulk density of about 0.2 to 0.6 g/mL and a particle size distribution such that the cumulative weight percent of the cellulose ester powder retained on Number 60, 80 100, 120, 140 and 200 sieves is:

| Sieve Number | Cumulative Weight Percent Retained |
|---|---|
| 60 | about 5 to 30 |
| 80 | about 10 to 40 |
| 100 | about 20 to 60 |
| 120 | about 36 to 75 |
| 140 | about 45 to 85 |
| 200 | about 60 to 92 | and the weight percent of cellulose ester powder which passes through a Number 325 sieve is not more than about 12 weight percent, and (2) a lubricant.

2. A composition according to claim 1 comprising (1) at least 30 weight percent of an ester of cellulose and residues of carboxylic acids having 2 to 4 carbon atoms having a degree of esterification of about 1.0 to 3.0 and (2) about 0.25 to 5.0 weight percent of a lubricant selected from the group consisting of talc, saturated fatty acids having about 16 to 20 carbon atoms, magnesium and calcium salts of saturated fatty acids having about 16 to 20 carbon atoms, alkali metal salts of aromatic carboxylic acids, silica, high molecular weight poly(alkylene glycols,), silicones, monoesters of propylene glycol and a saturated fatty acid containing about 8 to 22 carbon atoms, monoglycerides, mono/diglyceride mixtures, and alkali metal salts of esters of lactic acid and a saturated fatty acid containing about 8 to 22 carbon atoms.

3. A direct compression carrier composition comprising a compressible, free-flowing particulate composition comprising (1) cellulose acetate having a degree of esterification of about 1.6 to 3.0 and a viscosity of about 10 to 300 poises determined by ASTM Procedures D817 (Formula A) and D1343 in the form of a powder having a mean diameter of about 70 to 200 microns, a bulk density of about 0.2 to 0.6 g/mL and a particle size distribution such that the cumulative weight percent of the cellulose ester powder retained on Number 60, 80, 100, 120, 140 and 200 sieves is:

| Sieve Number | Cumulative Weight Percent Retained |
|---|---|
| 60 | about 5 to 30 |
| 80 | about 10 to 40 |
| 100 | about 20 to 60 |
| 120 | about 36 to 75 |
| 140 | about 45 to 85 |
| 200 | about 60 to 92 | and the weight percent of cellulose ester powder which passes through a Number 325 sieve is not more than about 12 weight percent and (2) a lubricant comprising a mixture of:
  (i) about 20 to 40 weight percent of monoglycerides or mono/diglyceride mixture having an iodine number of about 2 to 15;
  (ii) about 40 to 70 weight percent of a monoester of propylene glycol and a saturated fatty acid having about 16 to 20 carbon atoms;
  (iii) about 5 to 20 weight percent of an alkali metal salt of an ester of lactic acid and a saturated fatty acid having about 16 to 20 carbon atoms; and
  (iv) up to about 10 weight percent silica.

4. A composition according to claim 3 which contains up to about 1.0 weight percent of a wetting agent.

5. A direct compression carrier composition comprising a compressible, free-flowing particulate composition comprising (1) at least 80 weight percent cellulose acetate having a degree of esterification of about 2.2 to 2.6 and a viscosity of about 30 to 42 poises determined by ASTM Procedures D817 (Formula A) and D1343 in the form of a powder having a mean diameter of about 120 to 200 microns, a bulk density of about 0.3 to 0.4 g/mL and a particle size distribution such that the cumulative weight percent of the cellulose ester powder retained on Number 60, 80, 100, 120, 140 and 200 sieves is:

| Sieve Number | Cumulative Weight Percent Retained |
|---|---|
| 60 | about 5 to 15 |
| 80 | about 25 to 35 |
| 100 | about 35 to 55 |
| 120 | about 45 to 65 |
| 140 | about 55 to 75 |
| 200 | about 65 to 85 | and the weight percent of cellulose ester powder which passes through a Number 325 sieve is not more than about 7 weight percent and (2) about 0.5 to 2.0 weight percent of a lubricant composition comprising a mixture of:
  (i) about 25 to 35 weight percent of monoglycerides or mono/diglyceride mixture having an iodine number of about 2 to 15;
  (ii) about 50 to 60 weight percent of a monoester of propylene glycol and a saturated fatty acid having about 16 to 20 carbon atoms;
  (iii) about 12 to 18 weight percent of an alkali metal salt of an ester of lactic acid and a saturated fatty acid having about 16 to 20 carbon atoms; and
  (iv) up to about 5 weight percent silica; based on the total weight of the lubricant composition.

6. A composition according to claim 5 containing about 0.2 to 0.6 weight percent of an alkali metal salt of a sulfate of a saturated aliphatic alcohol containing about 8 to 22 carbon atoms.

7. A composition according to claim 5 containing about 0.2 to 0.6 weight percent of sodium lauryl sulfate.

8. A direct compression tableting composition comprising (1) the direct compression carrier composition of claim 1 and (2) a medicament.

9. A direct compression tableting composition comprising (1) the direct compression carrier composition of claim 3 and (2) a medicament.

10. A direct compression tableting composition comprising (1) the direct compression carrier composition of claim 3 and (2) at least 40 weight percent, based on the weight of the direct compression tableting composition, of a medicament.

11. A direct compression tableting composition comprising (1) the direct compression carrier composition of claim 3, (2) at least 40 weight percent, based on the weight of the direct compression tableting composition, of a medicament and (3) up to about 1.0 weight percent of a wetting agent.

12. A direct compression tableting composition comprising (1) the direct compression carrier composition of claim 3, (2) at least 40 weight percent, based on the weight of the direct compression tableting composition, of a medicament and (3) about 0.2 to 2.0 weight percent of an alkali metal salt of a sulfate of a saturated aliphatic alcohol containing about 8 to 22 carbon atoms.

13. A direct compression tableting composition comprising (1) the direct compression carrier composition of claim 5 and (2) a medicament.

14. A direct compression tableting composition comprising (1) the direct compression carrier composition of claim 5 and (2) at least 40 weight percent, based on the weight of the direct compression tableting composition, of a medicament.

15. A direct compression tableting composition comprising (1) the direct compression carrier composition of claim 5, (2) at least 40 weight percent, based on the weight of the direct compression tableting composition, of a medicament and (3) about 0.2 to 2.0 weight percent of an alkali metal salt of a sulfate of a saturated aliphatic alcohol containing about 8 to 22 carbon atoms.

16. A direct compression tableting composition comprising (1) the direct compression carrier composition of claim 5, (2) at least 40 weight percent, based on the weight of the direct compression tableting composition, of a medicament and (3) about 0.2 to 2.0 weight percent of sodium lauryl sulfate.

17. A medicinal tablet produced from the composition of claim 8.

18. A medicinal tablet produced from the composition of claim 9.

19. A medicinal tablet produced from the composition of claim 12.

20. A medicinal tablet produced from the composition of claim 15.

* * * * *